United States Patent
Berger et al.

[11] Patent Number: 5,152,899
[45] Date of Patent: Oct. 6, 1992

[54] PROCESS FOR THE ENRICHMENT OR SEPARATION OF ORGANIC SUBSTANCE MIXTURES

[75] Inventors: Joseph Berger, Basel; Thomas Feldkamp, Rheinfelden; Friedrich Lohse, Oberwil; Manfred Müller, Dagmersellen, all of Switzerland

[73] Assignee: Ciba-Geigy Corporation, Ardsley, N.Y.

[21] Appl. No.: 716,714

[22] Filed: Jun. 17, 1991

[30] Foreign Application Priority Data

Jun. 19, 1990 [CH] Switzerland .................. 2037/90

[51] Int. Cl.$^5$ .................. B01D 11/00; B01D 61/00
[52] U.S. Cl. .................. 210/644; 210/634; 210/653; 210/500.21; 210/649
[58] Field of Search .......... 210/644, 649, 651, 653, 210/638, 500.36, 321.74, 500.21, 500.25

[56] References Cited

U.S. PATENT DOCUMENTS

| | | | |
|---|---|---|---|
| 4,476,025 | 10/1984 | Chum et al. | 210/638 |
| 4,846,977 | 7/1989 | DeVellis et al. | 210/644 |
| 4,902,416 | 2/1990 | Schroeder et al. | 210/321.74 |

FOREIGN PATENT DOCUMENTS 239888 10/1987 European Pat. Off.

*Primary Examiner*—Robert A. Dawson
*Assistant Examiner*—Ana M. Fortuna
*Attorney, Agent, or Firm*—Kevin T. Mansfield; Edward McC. Roberts

[57] ABSTRACT

Salts of organic carboxylic acids can be separated from non-salt organic compounds using a semipermeable membrane consisting of a perfluorosulfonic acid polymer or a salt of such a polymer, by bringing a solution of the salts and the organic compounds in a $C_1$-$C_4$alkanol into contact with one side of the membrane and having the pure solvent on the opposite side of the membrane. The process can be used, for example, in purification processes or for recovering reactants from reaction residues.

18 Claims, No Drawings

PROCESS FOR THE ENRICHMENT OR SEPARATION OF ORGANIC SUBSTANCE MIXTURES

The present invention relates to a process for the enrichment or separation of salts of organic carboxylic acids from non-salt organic compounds, in which a solution of those salts and compounds in a low molecular weight alkanol is brought into contact with one side of a semipermeable membrane consisting of a perfluorosulfonic acid polymer, the pure low molecular weight alkanol being present on the opposite side of the membrane.

U.S. Pat. No. 4,846,977 describes a separating process for mixtures of polar and non-polar liquids using semipermeable membranes consisting of perfluorosulfonic acid polymers. Suitable polar liquids are, for example, lower alkanols and especially water, and suitable non-polar liquids are, for example, hydrocarbons, ethers, ketones, esters or organic acids.

It has surprisingly been found that using the same membranes it is also possible to enrich or separate mixtures of salts of organic carboxylic acids and non-salt organic compounds in the form of solutions in low molecular weight alkanols.

The invention relates to a process for the enrichment or separation of salts of organic carboxylic acids from non-salt organic compounds using a semipermeable membrane consisting of a perfluorosulfonic acid polymer or a salt of such a polymer, wherein a solution of the salts and organic compounds in an unsubstituted or $C_1$-$C_3$alkoxy-substituted $C_1$-$C_4$alkanol, mixtures of said alkanols or mixtures of said alkanols with ethers is brought into contact with one side of the membrane and the pure solvent is present on the opposite side of the membrane.

The concentration of the salts and organic compounds is preferably from 0.0001 to 10%, especially from 0.001 to 5% and more especially from 0.001 to 3% by weight, based on the solution.

The thickness of the membrane can be, for example, from 5 to 300 μm, preferably from 20 to 200 μm.

Perfluorosulfonic acid polymers and salts of those polymers are known and are described, for example, in U.S. Pat. No. 4,846,977. Some of those polymers are commercially available under the brand name NAFION® (DuPont).

In a preferred embodiment, the membrane consists of a perfluorosulfonic acid polymer having recurring structural elements of formula I

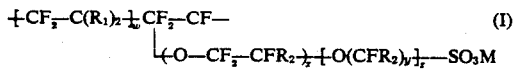

wherein $R_1$ and $R_2$ are each independently of the other F or $C_1$-$C_{10}$perfluoroalkyl, w is a number from 5 to 15, x is a number from 0 to 6, y is a number from 1 to 16, z is a number from 0 to 16, and M is $H^\oplus$, an ammonium cation or a metal cation, $R_1$ and $R_2$ are preferably fluorine or $C_1$-$C_3$perfluoroalkyl, especially fluorine or trifluoromethyl and more especially fluorine. In formula I, preferably w is a number from 5 to 10, x is a number from 0 to 2, y is a number from 1 to 6 and z is a number from 0 to 6, especially from 0 to 2.

M as an ammonium cation may be $NH_4^\oplus$ or an ammonium cation of a primary, secondary or tertiary open-chain amine having preferably from 1 to 20, especially from 1 to 12, carbon atoms, or an ammonium cation of a monocyclic or bicyclic secondary or tertiary amine or of a tricyclic tertiary amine having preferably from 4 to 12 carbon atoms.

M as a metal cation may be a mono- to tri-valent cation of a metal of the main and subsidiary groups, the transition metals and the noble metals. Mono- or divalent metal cations are preferred. Examples of metals are Li, Na, K, Rb, Cs, Mg, Ca, Sr, Ba, In, Sn, Pb, Cu, Ag, Au, Zn, Cd, Hg, Cr, Mo, Mn, Fe, Co, Ni, Rn, Rh, Pd, Ir, Pt, Sb, Bi, and also the group of the rare earth metals. Preferred metals are the alkali metals and alkaline earth metals, Cu, Ag, Au, Fe, Co, Ni, Zn, Cd and Mn.

In a preferred embodiment, M is $NH_4^\oplus$, an ammonium cation having a total of from 1 to 18 carbon atoms, or a mono- to tri-valent metal cation. M is more especially an alkali metal cation or $Ag^\oplus$.

The permeation of a salt of an organic carboxylic acid or of a non-salt organic compound can be influenced by the cation M chose. When membranes having relatively small monovalent cations are used, it is generally the non-salt compound that permeates preferentially. When relatively large mono- or poly-valent cations are used, it is generally the salt that permeates preferentially.

It has been found that in especially favourable cases the salt is retained virtually completely when M in formula I is $Ag^\oplus$. Conversely, the relatively non-polar organic compound is retained virtually completely when M in formula I is $Cs^\oplus$. Preference is therefore given to a process wherein M in formula I is $Ag^\oplus$ or $Cs^\oplus$.

The alkanol used as solvent contains from 1 to 4 carbon atoms and preferably from 1 to 3 carbon atoms. It may be substituted, for example by methoxy or ethoxy. Examples thereof are methanol, ethanol, n- and iso-propanol, n-, iso- and tert-butanol, methoxyethanol, ethoxyethanol, propoxyethanol, 1-methoxypropan-3-ol and 2-methoxypropan-1-ol. Preferred solvents are methanol, ethanol, 1- or 2-propanol and 2-methoxyethanol. It is also possible to use mixtures of alkanols with one another or with ethers, for example diethyl ether or ethylene glycol dimethyl ether.

The salt of the organic carboxylic acid may be an ammonium or metal salt, for example $NH_4^\oplus$, an ammonium cation of a primary, secondary or tertiary amine having a total of from 1 to 20 carbon atoms, an alkali metal salt or alkaline earth metal salt. Alkali metal salts and ammonium salts are preferred. $NH_4^\oplus$ and $Li^\oplus$ salts are especially preferred.

The organic carboxylic acid may be, for example, a mono-, di-, tri- or tetra-carboxylic acid. Aliphatic, cycloaliphatic, aromatic and heterocyclic or heteroaromatic monocarboxylic acids containing from 1 to 18 carbon atoms, preferably from 1 to 12 carbon atoms, are preferred.

In a preferred embodiment, the organic acid corresponds to formula (II)

wherein X is a direct bond, $C_1$-$C_4$alkylene, $C_2$-$C_4$alkylidene or $C_2$-$C_4$alkenylene, $R_3$ is H or $C_1$-$C_{12}$alkyl, $C_2$-$C_{12}$alkenyl, $C_2$-$C_{12}$alkynyl, $C_3$-$C_{12}$cycloalkyl, $C_3$-$C_{12}$cycloalkenyl, $C_6$-$C_{16}$aryl, $C_3$-$C_{12}$heterocycloalkyl, $C_3$-$C_{12}$heterocycloalkenyl, $C_6$-$C_{16}$heteroaryl, each of which is unsubstituted or substituted by —OH, —SH, —CN, —NO$_2$, halogen, C$_1$-C$_6$alkyl, C$_1$-C$_6$alkoxy, C$_1$-C$_6$alkylthio or by C$_1$-C$_6$alkyl-Y— in which Y is —CO—, —SO—, —SO$_2$—, —CO—O—, —O—CO—, —CO—NR$_4$R$_5$— or —NR$_4$R$_5$—CO—, and R$_4$ and R$_5$ are each independently of the other H, C$_1$-C$_6$alkyl, C$_2$-C$_4$hydroxyalkyl or R$_4$ and R$_5$ together are tetramethylene, pentamethylene or 3-oxapentyl-1,4-ene.

Examples of R$_3$ as alkyl, which may be linear or branched, are methyl, ethyl, n- and iso-propyl, n- and iso-butyl, pentyl, hexyl, heptyl, octyl, nonyl, decyl, undecyl and dodecyl.

Examples of R$_3$ as alkenyl, which may be linear or branched, are vinyl, crotonyl, allyl, but-1-en-1-yl, but-1-en-2-yl, but-1-en-3-yl, but-1-en-4-yl, but-2-en-1-yl, but-2-en-2-yl, but-2-en-4-yl, pentenyl, hexenyl, heptenyl, octenyl, nonenyl, decenyl, undecenyl and dodecenyl.

Examples of R$_3$ as alkynyl, which may be linear or branched, are ethynyl, prop-2-yn-1-yl, prop-2-yn-3-yl, butynyl, pentynyl, hexynyl, heptynyl, octynyl, decynyl and dodecynyl.

R$_3$ as cycloalkyl and cycloalkenyl preferably contains from 4 to 8 carbon atoms, especially 5 or 6 carbon atoms. Examples thereof are cyclopropyl and cyclopropenyl, cyclobutyl and cyclobutenyl, cyclopentyl and cyclopentenyl, cyclohexyl and cyclohexenyl, cycloheptyl and cycloheptenyl, cyclooctyl and cyclooctenyl.

R$_3$ as aryl preferably contains from 6 to 12 carbon atoms. Some examples thereof are phenyl, biphenyl and naphthyl.

R$_3$ as heterocycloalkyl and heterocycloalkenyl preferably contains from 4 to 8, especially from 4 to 6, ring carbon atoms. Preferred hetero atoms are those from the group O, S and NR$_6$ wherein R$_6$ is H, C$_1$-C$_6$alkyl or C$_1$-C$_7$acyl. R$_3$ as heteroaryl preferably contains from 4 to 11 ring carbon atoms and preferably hetero atoms from the group O, S and —N=. Some examples of heterocycles are pyrrolidine, tetrahydrofuran, tetrahydrothiophene, pyrroline, dihydrofuran, dihydrothiophene, indane, dihydrocoumarone, dihydrobenzothiophene, carbazole, dibenzofuran, dibenzothiophene, pyrazolidine, imidazolidine, pyrazoline, imidazoline, benzimidazolidine, oxazolidine, oxazoline, thiazolidine, thiazoline, isooxazolidine, isooxazoline, isothiazolidine, isothiazoline, benzoxazolidine, benzisooxazolidine, benzthiazolidine, 1,2,3- or 1,2,4-triazolidine, 1,2,3- or 1,2,4-triazoline, 1,2,3- or 1,2,4-oxazolidine or -oxazoline, piperidine, di- and tetra-hydropyridine, dihydro- and tetrahydro-pyran, di- and tetra-hydrothiopyran, piperazine, dehydropiperazine, morpholine, thiomorpholine, 1,3- and 1,4-dioxane, 1,4-dithiane, azepan, 1,3-dioxolane, 1,3-dithiolane, pyrrole, indole, imidazole, benzimidazole, furan, thiophene, benzofuran, benzothiophene, carbazole, dibenzofuran, dibenzothiophene, oxazole, isooxazole, thiazole, isothiazole, benzoxazole, benzothiazole, pyridine, pyrimidine, pyrazine, pyridazine, quinoline, isoquinoline, acridine, chromene, chromane, pyran, thiapyran, phenazine, phenoxazine, phenolthiazine and purine.

Examples of X in formula II are methylene, ethylene, 1,2- or 1,3-propylene, 1,2-, 1,3- or 1,4-butylene, ethylidene, 1,1- or 2,2-propylidene, 1,1- or 2,2-butylidene, ethenylene, prop-1-en-1,3- or -1,2- or -2,3-ylene.

In a preferred embodiment, the salt is a Li$^\oplus$ or NH$_4^\oplus$ salt of a carboxylic acid from the group furan-2-carboxylic acid, benzoic acid, methylbenzoic acid, phenylacetic acid, cinnamic acid, sorbic acid or a C$_2$-C$_8$alkanecarboxylic acid.

The non-salt organic compound preferably contains from 2 to 20, especially from 2 to 16 and more especially from 2 to 12, carbon atoms. The organic compound is especially an ester of an organic monocarboxylic acid having a total of from 2 to 16 carbon atoms, an ether having from 2 to 12 carbon atoms, a ketone having from 3 to 16 carbon atoms or an alcohol having from 5 to 16 carbon atoms.

In a preferred embodiment, the organic compound is a C$_1$-C$_6$alkyl ester of furan-2-carboxylic acid, benzoic acid, methylbenzoic acid, phenylacetic acid, cinnamic acid, sorbic acid or an C$_2$-C$_8$alkanecarboxylic acid; a C$_5$-C$_{12}$alkanol or benzyl alcohol; a dialiphatic ketone having from 3 to 10 carbon atoms, a C$_1$-C$_6$alkyl phenyl ketone, or diphenyl ketone; or a dialiphatic ether having from 2 to 8 carbon atoms, C$_1$-C$_6$alkyl phenyl ether, or diphenyl ether.

The membrane can be constructed in various forms for carrying out the process according to the invention and can be incorporated into separating modules of customary design. For example, flat membranes or asymmetric membranes can be combined to form two-chamber or multi-chamber systems. It is also possible to use tubular membranes or hollow fibres which are generally used in the form of bundles. In order to increase mechanical stability the membranes can be mounted on a supporting framework.

The process according to the invention is generally carried out at room temperature. In order to obtain a sufficient rate of flow it is advantageous to establish increased pressure on the solution side. The pressure is preferably from 1 to 10 MPa, more especially from 1 to 6 MPa. In a special embodiment, the process is carried out in accordance with the counter-current principle.

The process according to the invention can be used, for example, as an enrichment or purification process or for recovering or separating reactants or secondary products from reaction residues or reaction mixtures or for the isolation or purification of intermediates, especially when thermally unstable substances are involved.

The following Examples illustrate the invention in more detail.

EXAMPLES 1-37 a) Manufacture of the membranes

The starting material used is a commercially available polymeric perfluorosulfonic acid membrane (H form) (Nafion®-117, DuPont) that is approximately 200 μm thick. For the purpose of conversion into the salt form, the membrane is placed for 1 to 30 days in a 1:1 mixture consisting of methanol and a 1M aqueous solution of the hydroxide or chloride of the desired cation. The membrane is then washed with distilled water and methanol. Before use, the membrane is placed in the respective solvent until equilibrium swelling has taken place (1 to 5 days). For the manufacture of membranes having silver cations, sodium salts of the perfluorosulfonic acid membrane are used as starting material and are reacted with silver nitrate.

b) Permeation tests

In the centre of a pressure cell, the membrane (diameter 4.7 cm) is mounted in the holder. Each chamber is connected to a reservoir for the solution or the pure solvent to which a pump is connected. The reservoirs are mounted on scales. Between the reservoirs and the pumps there are arranged conductivity cells and between the outlet and the reservoirs there are arranged UV detectors. A pressure of 2.5 MPa is established on the solvent side and the solution and the solvent are circulated in the same direction. $^{14}C$ measurements are taken using a liquid scintillation detector. The measurement data are evaluated using a computer program. The detectors are each calibrated with the organic compound and the salt of the carboxylic acid and the calibration curves are converted into algorithms from which the desired data are calculated.

The selectivity S is defined as follows, $G^P$ being the proportion by weight in the permeate and $G^L$ being the proportion by weight in the solution:

$$S = \frac{G^P \text{ (relatively non-polar organic compound)}/G^P \text{ (carboxylic acid salt)}}{G^L \text{ (reatively non-polar organic compound)}/G^L \text{ (carboxylic acid salt)}}$$

Further data can be found in Tables 1 and 2 below.

TABLE 1

| Example No. | Metal cation in the membrane | Solvent | Carboxylic acid salt | Relatively non-polar organic compound |
|---|---|---|---|---|
| 1 | Li⊕ | methanol | Li cinnamate | methyl cinnamate |
| 2 | Li⊕ | methanol | Li cinnamate | methyl cinnamate |
| 3 | Li⊕ | methanol | Li cinnamate | methyl cinnamate |
| 4 | Li⊕ | methanol | Li cinnamate | methyl cinnamate |
| 5 | Li⊕ | methanol | Li cinnamate | methyl cinnamate |
| 6 | Li⊕ | methanol | Li cinnamate | methyl cinnamate |
| 7 | Li⊕ | methanol | Li cinnamate | methyl cinnamate |
| 8 | Li⊕ | methanol | Li cinnamate | methyl cinnamate |
| 9 | Li⊕ | methanol | Li cinnamate | methyl cinnamate |
| 10 | Li⊕ | methanol | Li cinnamate | furan-2-carboxylic acid ethyl ester |
| 11 | Li⊕ | methanol | Li cinnamate | benzyl alcohol |
| 12 | Li⊕ | methanol | p-toluic acid Li salt | p-toluic acid ethyl ester |
| 13 | Li⊕ | methanol | phenylacetic acid Li salt | phenylacetic acid methyl ester |
| 14 | Li⊕ | methanol | benzoic acid Li salt | benzoic acid methyl ester |
| 15 | Li⊕ | methanol | sorbic acid Li salt | sorbic acid ethyl ester |
| 16 | Li⊕ | methanol | Li cinnamate | acetophenone |
| 17 | Li⊕ | methanol | Li cinnamate | methyl phenyl ether |
| 18 | Li⊕ | methanol | Li acetate | methyl acetate |
| 19 | Li⊕ | 2-methoxyethanol | Li cinnamate | methyl cinnamate |
| 20 | Na⊕ | methanol | Li cinnamate | methyl cinnamate |
| 21 | Na⊕ | ethanol | Li cinnamate | methyl cinnamate |
| 22 | K⊕ | methanol | Li cinnamate | methyl cinnamate |
| 23 | K⊕ | methanol | Li cinnamate | methyl acetate |
| 24 | Ag⊕ | methanol | Li cinnamate | methyl cinnamate |
| 25 | Ag⊕ | methanol | Li cinnamate | methyl cinnamate |
| 26 | Cs⊕ | methanol | Li cinnamate | methyl cinnamate |
| 27 | Cs⊕ | methanol | Li cinnamate | methyl cinnamate |
| 28 | $Ni^{2\oplus}$ | methanol | Li cinnamate | methyl cinnamate |
| 29 | $Co^{2\oplus}$ | methanol | Li cinnamate | methyl cinnamate |
| 30 | $Cu^{2\oplus}$ | methanol | Li cinnamate | methyl cinnamate |
| 31 | $NH_4^\oplus$ | methanol | Li cinnamate | methyl cinnamate |
| 32 | $N(C_4H_9)_4^\oplus$ | methanol | Li cinnamate | methyl cinnamate |
| 33 | quinuclidinium (1-azabicyclo[2.2.2]octane) | methanol | Li cinnamate | methyl cinnamate |
| 34 | Li⊕ | methanol/diethylene glycol dimethyl ether 1:1 | ammonium benzoate | methyl acetate |
| 35 | Li⊕ | methanol | Li benzoate | acetophenone |
| 36 | Li⊕ | methanol | ammonium benzoate | methyl benzoate |
| 37 | Li⊕ | methanol | Li cinnamate | methyl cinnamate |
| 38 | Li⊕ | methanol | octylammonium cinnamate | methyl cinnamate |
| 39 | octylammonium⊕ | methanol | Li cinnamate | methyl cinnamate |
| 40 | Li⊕ | methanol | di-Li phthalate[1] | methyl benzoate |
| 41 | Li⊕ | methanol | di-Li phthalate[1] | tris(2-ethylhexyl)trimellitate |
| 42 | Li⊕ | methanol | tri-Li trimellitate[2] | dimethyl phthalate |
| 43 | Li⊕ | methanol | tetra-Li pyromellitate[3] | methyl benzoate |
| 44 | Li⊕ | methanol | di-Li 2-carboxycinnamate[4] | methyl cinnamate |

[1] 98% dilithium salt + 2% monolithium salt
[2] 35% trilithium salt + 65% dilithium salt
[3] 45% tetralithium salt + 55% trilithium salt
[4] 65% dilithium salt + 35% monolithium salt

TABLE 2

| Example No. | Permeation rate (mg·min⁻¹·cm⁻²) | Detection [UV (nm)/ C 14] | Carboxylic acid salt (amount start of test) Amount (mg) | Carboxylic acid salt (amount start of test) Conc. (wt. %) | Relatively non-polar organic comp. (amount start of test) Amount (mg) | Relatively non-polar organic comp. (amount start of test) Conc. (wt. %) | Test time (min.) | Test end: Amounts of components in permeate (mg) Salt | Test end: Amounts of components in permeate (mg) Organic compound | Selectivity |
|---|---|---|---|---|---|---|---|---|---|---|
| 1 | 1.675 | 305 | 48.75 | 0.00975 | 1.25 | 0.00025 | 1080 | 0.714 | 0.340 | 18.7 |
| 2 | 1.583 | 305 | 45.00 | 0.00900 | 5.00 | 0.00100 | 1080 | 0.280 | 0.342 | 11.0 |
| 3 | 1.737 | 305 | 35.00 | 0.00700 | 15.00 | 0.00300 | 1050 | 0.425 | 1.005 | 5.5 |
| 4 | 1.721 | 305 | 25.00 | 0.00500 | 25.00 | 0.00500 | 1080 | 0.399 | 1.321 | 3.3 |
| 5 | 1.725 | 305 | 15.00 | 0.00300 | 35.00 | 0.00700 | 1080 | 0.300 | 1.864 | 2.7 |
| 6 | 1.741 | 305 | 5.00 | 0.00100 | 45.00 | 0.00900 | 1080 | 0.159 | 2.484 | 1.7 |
| 7 | 1.749 | 305 | 1.25 | 0.00025 | 48.75 | 0.00975 | 1050 | 0.044 | 2.828 | 1.6 |
| 8 | 1.767 | 305 | 5.00 | 0.00100 | 5.00 | 0.00100 | 1080 | 0.085 | 0.276 | 3.3 |
| 9 | 1.732 | 305 | 250.00 | 0.05000 | 250.00 | 0.05000 | 1080 | 4.176 | 12.974 | 3.1 |
| 10 | 1.232 | 260 | 250.00 | 0.05000 | 250.00 | 0.05000 | 1080 | 2.379 | 14.467 | 6.1 |
| 11 | 1.207 | 260 | 250.00 | 0.05000 | 250.00 | 0.05000 | 1080 | 2.173 | 34.200 | 15.7 |
| 12 | 1.685 | 255 | 25.00 | 0.00500 | 25.00 | 0.00500 | 1080 | 0.495 | 1.473 | 3.0 |
| 13 | 1.653 | 250 | 250.00 | 0.05000 | 250.00 | 0.05000 | 1080 | 4.617 | 18.687 | 4.1 |
| 14 | 1.690 | 255 | 250.00 | 0.05000 | 250.00 | 0.05000 | 1080 | 4.465 | 19.138 | 4.3 |
| 15 | 1.680 | 275 | 75.00 | 0.00500 | 75.00 | 0.00500 | 1050 | 0.787 | 1.506 | 1.9 |
| 16 | 0.717 | 280 | 250.00 | 0.05000 | 250.00 | 0.05000 | 1080 | 2.165 | 17.186 | 7.9 |
| 17 | 1.083 | 280 | 250.00 | 0.00500 | 250.00 | 0.05000 | 1040 | 2.187 | 14.878 | 6.8 |
| 18 | 1.284 | C 14 | 7.50 | 0.00500 | 7.50 | 0.00500 | 1320 | 0.260 | 1.980 | 10.0 |
| 19 | 0.350 | 310 | 125.00 | 0.02500 | 125.00 | 0.02500 | 270 | 0.194 | 0.381 | 2.0 |
| 20 | 0.563 | 305 | 25.30 | 0.00500 | 25.30 | 0.00500 | 1080 | 0.170 | 0.569 | 3.4 |
| 21 | 0.067 | 300 | 25.00 | 0.00500 | 25.00 | 0.00500 | 1080 | 0.010 | 0.171 | 18.0 |
| 22 | 0.024 | 305 | 25.30 | 0.00500 | 25.30 | 0.00500 | 3240 | 0.295 | 0.443 | 1.5 |
| 23 | 0.010 | C 14 | 10.00 | 0.00500 | 10.00 | 0.00500 | 5730 | 0.049 | 0.302 | 6.5 |
| 24 | 0.358 | 305 | 25.30 | 0.00500 | 25.30 | 0.00500 | 6500 | 0.000 | 7.400 | ∞ |
| 25 | 0.189 | 305 | 1500.00 | 1.00000 | 3000.00 | 2.00000 | 1080 | 0.146 | 37.044 | 253.7 |
| 26 | 0.020 | 305 | 25.30 | 0.00500 | 25.30 | 0.00500 | 3600 | 0.390 | 0.000 | 0.0 |
| 27 | 0.037 | 305 | 1500.00 | 1.00000 | 1500.00 | 1.00000 | 260 | 0.234 | 0.000 | 0.0 |
|  |  |  |  |  |  |  | 340 | 0.260 | 0.077 | 0.3 |
| 28 | 0.031 | 305 | 25.30 | 0.00500 | 25.30 | 0.00500 | 2400 | 0.327 | 0.071 | 0.2 |
| 29 | 0.033 | 305 | 25.30 | 0.00500 | 25.30 | 0.00500 | 3510 | 0.772 | 0.466 | 0.6 |
| 30 | 0.064 | 305 | 25.30 | 0.00500 | 25.30 | 0.00500 | 2700 | 0.042 | 1.842 | 0.3 |
| 31 | 0.604 | 305 | 25.30 | 0.00500 | 25.00 | 0.00500 | 1080 | 0.331 | 0.719 | 2.2 |
| 32 | 0.314 | 305 | 25.30 | 0.00500 | 25.00 | 0.00500 | 1080 | 0.032 | 0.512 | 16.1 |
| 33 | 0.090 | 305 | 25.30 | 0.00500 | 25.00 | 0.00500 | 1080 | 0.040 | 0.116 | 2.9 |
| 34 | 0.352 | C 14 | 10.00 | 0.00500 | 10.00 | 0.00500 | 4350 | 1.880 | 3.780 | 2.6 |
| 35 | 0.945 | 255 | 250.00 | 0.05000 | 250.00 | 0.05000 | 1350 | 1.586 | 15.854 | 10.0 |
| 36 | 1.740 | 255 | 250.00 | 0.05000 | 250.00 | 0.05000 | 1680 | 8.839 | 29.195 | 3.3 |
| 37 | 1.422 | 305 | 5000.00 | 1.0000 | 5000.00 | 1.00000 | 60 | 4.800 | 7.672 | 1.6 |
| 38 | 1.483 | 305 | 25.00 | 0.00500 | 25.00 | 0.00500 | 2070 | 1.024 | 3.093 | 3.3 |
| 39 | 1.099 | 305 | 25.00 | 0.00500 | 25.00 | 0.00500 | 2040 | 0.441 | 2.602 | 6.5 |
| 40 | 1.400 | 270 | 75.00 | 0.01500 | 75.00 | 0.01500 | 2040 | 1.216 | 14.340 | 14.3 |
| 41 | 1.392 | 270 | 75.00 | 0.01500 | 75.00 | 0.01500 | 2040 | 1.547 | 10.779 | 8.0 |
| 42 | 1.464 | 270 | 75.00 | 0.01500 | 75.00 | 0.01500 | 2040 | 1.601 | 13.096 | 9.7 |
| 43 | 1.587 | 270 | 2.50 | 0.00050 | 2.50 | 0.00050 | 2520 | 0.001 | 0.105 | 109.6 |
| 44 | 1.563 | 305 | 75.00 | 0.01500 | 75.00 | 0.01500 | 2040 | 1.434 | 9.361 | 7.3 |

What is claimed is:

1. A process for the enrichment of salts of organic carboxylic acids from non-salt organic compounds using a semipermeable membrane consisting of a perfluorosulfonic acid polymer or a salt of such a polymer, wherein the process comprises:
   contacting one side of the membrane with a solution of said salts and non-salt organic compounds in a solvent selected from an unsubstituted or $C_1$-$C_3$ alkoxy-substituted $C_1$-$C_4$ alkanol, a mixture of said alkanols, or a mixture of said alkanols with ethers;
   contacting the opposite side of the membrane with a solvent which is the same solvent selected to be present in the in said solution of salts and non-salt organic compounds;
and collecting the enriched or separated salts at one side of the membrane by preferentially permeating either the salts of organic carboxylic acids or the non-salt organic compound through the membrane.

2. A process according to claim 1, wherein the concentration of the salts and organic compounds is from 0.0001 to 10% by weight, based on the solution.

3. A process according to claim 1, wherein the membrane has a thickness of from 5 to 300 μm.

4. A process according to claim 1, wherein the membrane consists of a perfluorosulfonic acid polymer having recurring structural elements of formula I

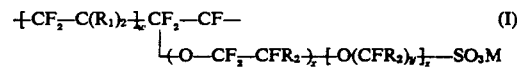

wherein $R_1$ and $R_2$ are each independently of the other F or $C_1$-$C_{10}$perfluoroalkyl, w is a number from 5 to 15, x is a number from 0 to 6, y is a number from 1 to 16, z is a number from 0 to 16, and M is $H^⊕$, an ammonium cation or a metal cation.

5. A process according to claim 4, wherein M is $NH_4^⊕$, an ammonium cation having a total of from 1 to 18 carbon atoms, or a mono- to tri-valent metal cation.

6. A process according to claim 4, wherein M is an alkali metal cation or $Ag^⊕$.

7. A process according to claim 1, wherein the solvent is methanol, ethanol, 1- or 2-propanol or 2-methoxyethanol.

8. A process according to claim 1, wherein the organic carboxylic acid salt is an ammonium or metal salt.

9. A process according to claim 8, wherein the salt is an alkali metal salt or an ammonium salt.

10. A process according to claim 8, wherein the salt is a $NH_4^\oplus$ salt or $Li^\oplus$ salt.

11. A process according to claim 1, wherein the organic carboxylic acid forming the salt is an aliphatic, cycloaliphatic, aromatic, heterocyclic or heteroaromatic monocarboxylic acid having from 1 to 18 carbon atoms.

12. A process according to claim 11, wherein the organic acid corresponds to formula (II)

$$R_3-X-COOH \quad (II)$$

wherein X is a direct bond, $C_1$-$C_4$alkylene, $C_2$-$C_4$alkylidene or $C_2$-$C_4$alkenylene, $R_3$ is H or $C_1$-$C_{12}$alkyl, $C_2$-$C_{12}$alkenyl, $C_2$-$C_{12}$alkynyl, $C_3$-$C_{12}$cycloalkyl, $C_3$-$C_{12}$cycloalkenyl, $C_6$-$C_{16}$aryl, $C_3$-$C_{12}$heterocycloalkyl, $C_3$-$C_{12}$heterocycloalkenyl, $C_6$-$C_{16}$heteroaryl, each of which is unsubstituted or substituted by —OH, —SH, —CN, —NO$_2$, halogen, $C_1$-$C_6$alkyl, $C_1$-$C_6$alkoxy, $C_1$-$C_6$alkylthio or by $C_1$-$C_6$alkyl—Y— in which Y is —CO—, —SO—, —SO$_2$—, —CO—O—, —O—CO—, —CO—NR$_4$R$_5$— or —NR$_4$R$_5$—CO—, and $R_4$ and $R_5$ are each independently of the other H, $C_1$-$C_6$alkyl, $C_2$-$C_4$hydroxyalkyl or $R_4$ and $R_5$ together are tetramethylene, pentamethylene or 3-oxapentyl-1,4-ene.

13. A process according to claim 1, wherein the salt is a $Li^\oplus$ or $NH_4^\oplus$ salt of a carboxylic acid selected from the group consisting of furan-2-carboxylic acid, benzoic acid, methylbenzoic acid, phenylacetic acid, cinnamic acid, sorbic acid and a $C_2$-$C_8$alkanecarboxylic acid.

14. A process according to claim 1, wherein the non-salt organic compound is an ester of an organic monocarboxylic acid having a total of from 2 to 16 carbon atoms, an ether having from 2 to 12 carbon atoms, a ketone having from 3 to 16 carbon atoms or an alcohol having from 5 to 16 carbon atoms.

15. A process according to claim 14, wherein the non-salt organic compound is a $C_1$-$C_6$alkyl ester of furan-2-carboxylic acid, benzoic acid, methylbenzoic acid, phenylacetic acid, sorbic acid or a $C_2$-$C_8$alkanecarboxylic acid; a $C_5$-$C_{12}$alkanol or benzyl alcohol; a dialiphatic ketone having from 3 to 10 carbon atoms, a $C_1$-$C_6$alkyl phenyl ketone, or diphenyl ketone; or a dialiphatic ether having from 2 to 8 carbon atoms, $C_1$-$C_6$alkyl phenyl ether, or diphenyl ether.

16. A process according to claim 1 wherein said process is carried out at room temperature.

17. A process according to claim 1 wherein a pressure of from 1 MPa to 10 MPa is established on the solution side.

18. A process according to claim 1 wherein said process is carried out in counter-current mode.

* * * * *